United States Patent
Kloor et al.

(10) Patent No.: US 9,566,319 B2
(45) Date of Patent: Feb. 14, 2017

(54) P16$^{INK4a}$ DERIVED PEPTIDES FOR PROPHYLAXIS AND THERAPY OF HPV-ASSOCIATED TUMORS AND OTHER P16$^{INK4a}$ EXPRESSING TUMORS

(71) Applicant: Ruprecht-Karls-Universität Heidelberg, Heidelberg (DE)

(72) Inventors: Matthias Kloor, Ludwigshafen (DE); Miriam Reuschenbach, Heidelberg (DE); Magnus Von Knebel-Doeberitz, Heidelberg (DE)

(73) Assignee: Ruprecht-Karls-Universitaet Heidelberg, Heidelberg (DE)

( * ) Notice: Subject to any disclaimer, the term of this patent is extended or adjusted under 35 U.S.C. 154(b) by 0 days.

(21) Appl. No.: 14/800,586

(22) Filed: Jul. 15, 2015

(65) Prior Publication Data
US 2015/0313979 A1 Nov. 5, 2015

Related U.S. Application Data

(62) Division of application No. 13/714,273, filed on Dec. 13, 2012, now Pat. No. 9,114,101.

(51) Int. Cl.
*C07K 14/00* (2006.01)
*A61K 39/00* (2006.01)
*C12N 15/86* (2006.01)

(52) U.S. Cl.
CPC ........... *A61K 39/0011* (2013.01); *C12N 15/86* (2013.01); *A61K 2039/53* (2013.01)

(58) Field of Classification Search
None
See application file for complete search history.

(56) References Cited

PUBLICATIONS

Azuma, et al.; "Identification of HER2/neu-derived Peptides Capable of Inducing Both Cellular and Humoral Immune Responses in HLA-A24 Positive Breast Cancer Patients"; Breast Cancer Research and Treatment; vol. 86, pp. 19-29 (2004).
http://clinicaltrials.gov/ct2/show/NCT01462838; "Immune Therapy of HPV-induced Cancers"; (Oct. 2011).
Reuschenbach, et al.; "Characterization of Humoral Immune Responses Against p16, p53, HPV16 E6 and HPV16 E7 in Patients with HPV-Associated Cancers"; Int. J. Cancer; vol. 123, pp. 2626-2631 (2008).
Hernandez; Generation of HBsAg(S) Particles Carrying Combined HPV-16E7 and p16INK4a Epitopes and Their Immunogenicity in Vitro; Abstract of PhD thesis (Jul. 19, 2011).
Wentzensen, et al.; "P16INK4a is a Tumor Autoantigen in HR-HPV Induced Cancers"; Annual Meeting of the American Association for Cancer Research; vol. 46 (2005).
Reuschenbach, et al.: "Abstract #735: Natural and in vitro primed T cell reactivity against p16INK4a support future active immunization of cervical cancer patients with this antigen". 100th AACR Annual Meeting, Apr. 18-22, 2009.
Freshney, R. Ian, "Culture of Animal Cells, A Manual of Basic Technique", Alan R. Liss, Inc., 1983, New York, p. 4.
Dermer, Gerald B., "Another Anniversary for the War on Cancer", Bio/Technology, 1994 vol. 12: p. 320.
Spitler, Lynn E., "Cancer Vaccines: The Interferon Analogy". Cancer Biotherapy, 1995, vol. 10, No. 1, p. 1-3.
Gura, Trish, Systems for Identifying New Drugs are Often Faulty, Science 1997, vol. 278, p. 1041-1042.
Ezzell, Carol, "Cancer "Vaccines": An Idea Whose Time Has Come?" Journal of NIH Research, 1995, vol. 7, p. 46-49.
Boon, Thierry, "Toward a Genetic Analysis of Tumor Rejection Antigens", Advances in Cancer Research, 1992, vol. 58, pp. 177-210.
Jain, Rakesh K., "Barriers to Drug Delivery in Solid Tumors", Scientific American, 1994, vol. 271, pp. 58-65.
Haigh, et al., "Vaccine Therapy for Patients with Melanoma", Oncology, 1999, vol. 13, No. 11, pp. 1561-1582.
Burgess, et al., "Possible Dissociation of the heparin-binding and Mitogenic Activities of Heparin-binding (acidic Fibroblast) Growth Factor-1 from Its Receptor-binding Activities by Site-directed Mutagenesis of a Single Lysine Residue" Journal of Cell Biology, vol. 111, Nov. 1990, 2129-2138.
Lazar, et al., "Transforming Growth Factor a: Mutation of Aspartic Acid 47 and Leucine 48 Results in Different Biological Activities" Molecular and Cellular Biology, Mar. 1988, vol. 8, No. 3, 1247-1252.
Lin, et al., Structure-Function Relationships in Glucagon: properties of Highly Purified Des-His 1-, Monoiodo-, and [Des-Asn28, Thr 29 (homserine lactone 27)-glucagonBiochemistry USA, vol. 14: pp. 1559-1563 (1975).
Schwartz, et al., "A superactive insulin: [B10-Aspartic acid]insulin (human)", Proc. Natl Acad Sci USA, vol. 84, pp. 6408-6411 (1987).

*Primary Examiner* — Sheela J Huff
(74) *Attorney, Agent, or Firm* — Perkins Coie LLP; Viola T. Kung

(57) ABSTRACT

Described are particular fragments of the cyclin-dependent kinase inhibitor p16 capable of increasing IFN-γ secretion of T cells or inducing proliferation of T cells and the use of said fragments for immunizing an individual against HPV-associated or other p16$^{INK4a}$ expressing carcinomas, preferably advanced carcinomas.

7 Claims, 5 Drawing Sheets

P16$^{INK4a}$ DERIVED PEPTIDES FOR PROPHYLAXIS AND THERAPY OF HPV-ASSOCIATED TUMORS AND OTHER P16$^{INK4a}$ EXPRESSING TUMORS

This application is a divisional application of U.S. application Ser. No. 13/714,273, filed Dec. 13, 2012. The contents of the above-identified application is incorporated herein by reference in its entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Mar. 27, 2013, and a size of 3.05 kilobytes. The Sequence Listing filed via EFS-Web is part of the specification and is hereby incorporated in its entirety by reference herein.

TECHNICAL FIELD

The present invention relates to particular fragments of the cyclin-dependent kinase inhibitor p16$^{INK4a}$ and the use of said fragments for immunizing an individual against p16$^{INK4a}$-expressing tumors.

BACKGROUND OF THE INVENTION

Several million people fall ill with, and die of, carcinomas world-wide every year. These mortality rates have remained unchanged for many years despite intensive therapy research. Until now, patients suffering from carcinomas often have to undergo carcinoma-removing surgery or chemotherapy or radiation therapy. However, this is accompanied by very massive side-effects which then contribute to the mortality rates of patients suffering from carcinomas. Interestingly, human papillomaviruses (HPV) are associated with the development of over 5% of all cancers (Parkin and Bray, 2006). Prophylactic HPV vaccination is already available but shows no therapeutic effects in already infected people (Hildesheim et al., 2007). Thus, there is a need of novel treatment options.

SUMMARY OF THE INVENTION

It is the object of the present invention to provide a means for therapy and prophylaxis of HPV-associated tumors and other p16$^{INK4a}$ expressing tumors.

According to the invention this is achieved by the subject matters defined in the claims. The studies leading to the present invention emanated from the observation that the cellular protein p16$^{INK4}$ is expressed in HPV infected cells when the cells achieve a transformed and possibly malignant phenotype due to the disruption of a negative feedback loop by the HPV oncogene product E7 (Sano et al., 1998; Klaes et al., 2001). Thus, p16$^{INK4a}$ is strongly expressed in virtually all HPV-induced carcinomas and high grade pre-neoplasias, including cervical, vulvar, vaginal, penile, anal and head and neck tumors (Ishikawa et al., 2006; Samama et al., 2006; Missaoui et al., 2006; Santos et al., 2006; Roma et al., 2008; Hafkamp et al., 2003). Under physiological conditions p16$^{INK4}$ is only expressed in cells that undergo subsequent senescence and, thus, is barely found expressed in normal tissues (Beauséjour et al., 2007). Besides the HPV-oncogene driven p16$^{INK4a}$-expression in HPV-associated tumors, p16$^{INK4a}$ is found also overexpressed in various tumors not associated with an HPV infection or in tumors where HPV has been found but a viral carcinogenesis is not proven, including a fraction of melanoma and non-melanoma skin cancers (Nindl et al., 2004; Busch et al., 2010), lung cancers (Leversha et al., 2003; Esposito et al., 2004), esophageal, gastric and colorectal cancers (Ding et al., 2010; Kim et al., 2005) and kidney, bladder, ovarian, endometrial and breast cancers (Ikuerowo et al. 2007; Buza et al., 2010; Giordano et al., 2008; Giordano et al., 2007; di Vinci et al., 2005). It is known that mutations of the retinoblastoma tumor suppressor gene result in upregulation of p16$^{INK4a}$ expression (Okamoto et al., 1994). However, the underlying mechanisms for the strong p16INK4a expression in these instances are most likely more heterogenic and not finally understood.

Overexpression of endogenous gene-products in cancer cells has since long been recognized as a valuable source for tumor associated antigens. Immune responses against such antigens have been observed in various cancer patients and have been increased in immunotherapeutic trials (Jäger et al., 2003; Finn, 2008; Rescigno et al., 2007).

During the experiments leading to the present invention it could be demonstrated that T lymphocytes isolated from peripheral blood samples of healthy individuals can be specifically stimulated in vitro with p16$^{INK4a}$ derived peptides and that CD4+ and CD8+ T cells from cervical cancer patients show spontaneous reactivity against the same p16$^{INK4a}$ peptide and give rise to cytotoxic T cell lines that are able to attack and kill co-cultured HLA-matched p16$^{INK4a}$ loaded cells and cervical cancer cell lines. In other words, fragments of p16$^{INK4}$ are highly immunogenic inducing a very strong immune response against p16$^{INK4}$. Further, it has been demonstrated that also humoral immune responses are detectable against p16$^{INK4a}$.

The described expression pattern of p16$^{INK4}$ and the finding of spontaneous immune responses against p16$^{INK4}$ that are not associated with any autoimmune diseases make p16$^{INK4}$ a promising candidate for immunization of patients with p16$^{INK4a}$ expressing cancers. An actively induced strong immune response against p16$^{INK4}$ could specifically destroy HPV-transformed cells and other p16$^{INK4a}$-expressing cancer cells. Vaccination of donor T cells with these p16$^{INK4}$ peptides was performed in cell culture experiments. Additional experiments using the p16$^{INK4}$ peptides revealed spontaneous T cell responses in cervical cancer patients confirming that particular p16$^{INK4}$ peptides are immunogenic also in vivo. Thus, prophylaxis or therapy of cancer based on immunization using these peptides should have several benefits for a patient. p16$^{INK4}$ is strongly expressed in all HPV-associated cancers irrespective of the HPV type and in various other cancer types. Severe side effects of p16$^{INK4}$ immunization are not expected, because p16$^{INK4}$ is barely expressed in normal tissues and no autoimmune phenomena have been observed in individuals with spontaneous immune responses against p16$^{INK4}$. Finally, immune evasion due to antigen loss is very unlike, because p16$^{INK4}$ expression is intricately linked to the malignant phenotype of the tumor cell.

The spot count is normalized by subtracting background spot detection in wells without peptides. In B the increased spot count in cells stimulated with the peptides p16INK4a_37-63, p16INK4a_51-80 and p16INK4a_73-104 compared to day 0 becomes clear. CEF=CMV, EBV, influenza (flu) peptide mix positive control.

Figure 2:
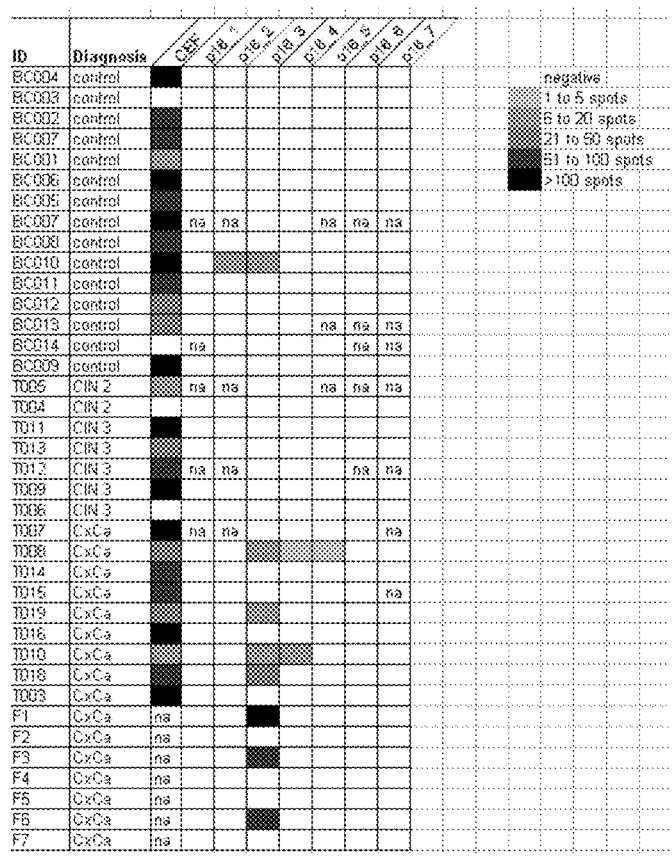

FIG. 2 shows ELISpot (interferon gamma) results in 23 patients (Tx and Fx) and 15 healthy controls (BCx) against the positive control virus mix (CEF) and against the seven 30mer p16$^{INK4a}$ peptides (Table 1).

Results are background adjusted and only spots above the cut-off (2 times the spots in the negative control well+2 standard deviations of reactivity against the respective p16$^{INK4a}$ peptide) are considered. Two individuals had CD4$^+$ responses, the remaining had CD8$^+$ responses. na=not analyzed.

Figure 3:
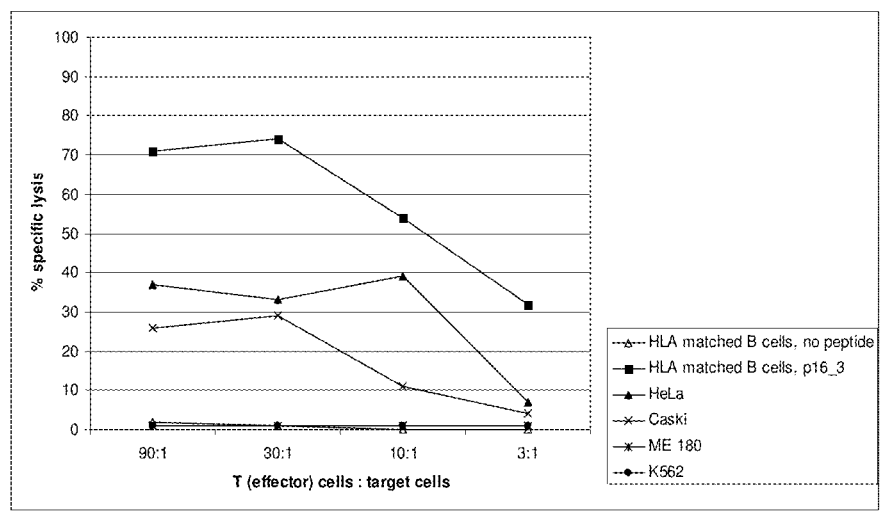

FIG. 3 shows Chromium release assay.

CD8 T cells from a cervical cancer patient (HLA A2 A3 B7 B15 Cw3 Cw7) induce lysis of HLA-matched B cells loaded with p16INK4a_37-63 (black squares) but not of the same B cells without the p16$^{INK4a}$ peptide (open triangles). Cervical cancer cell lines HeLa (p16$^{INK4a}$+, HLA A68, B15, B95, Cw7 Cw12) and Caski (p16$^{INK4a}$+, HLA A2, A3, B7, B37, Cw5, Cw7) are lysed while no lysis of ME180 and K562 is detected.

Figure 4:
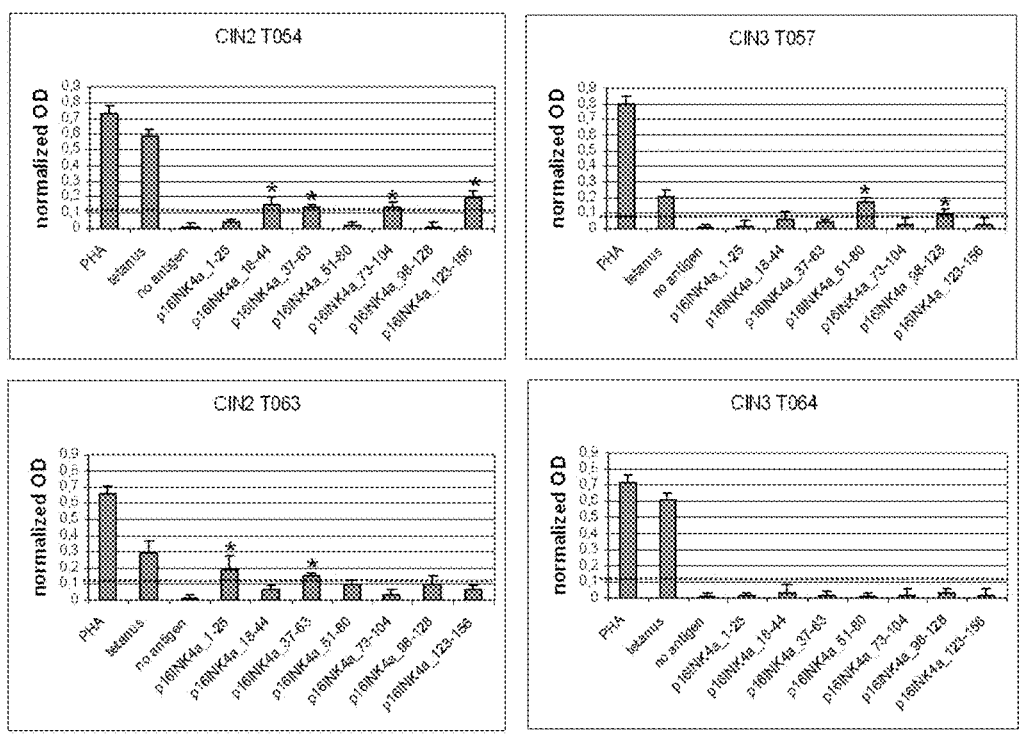

FIG. 4 shows proliferation of peripheral blood mononuclear cells from women with cervical dysplasias after stimulation with the seven p16INK4a peptides (Table 1).

Shown are optical densities of the BrdU proliferation assay performed after incubation of PBMCs with p16INK4a peptides, positive controls (mitogen PHA and tetanus toxoid) and negative controls (no antigen). Dashed lines indicate cut-off for positive response. Asterisks indicate proliferation inducing p16INK4a peptides. Shown are the results from three reacting patients and one negative patient.

Figure 5:
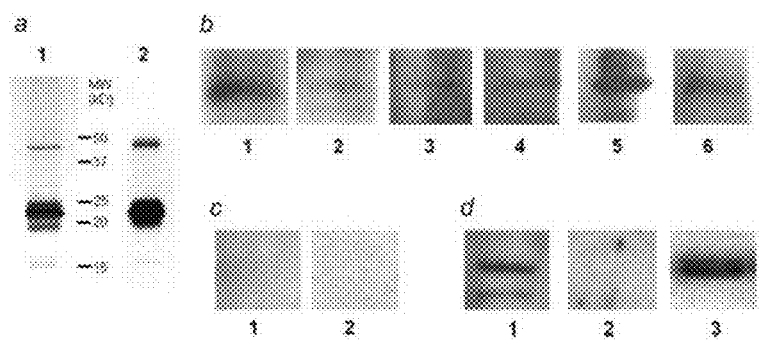

FIG. 5 shows erological p16$^{INK4a}$ reactivity in Western blot.

(a) (1) Silver stain of purified His-tagged p16$^{INK4a}$. (2) Western blot of purified His-tagged p16$^{INK4a}$ with the monoclonal p16$^{INK4a}$ antibody E6H4.

(b) 6 representative positive sera are shown. The protein size corresponds to the reaction of the monoclonal antibody (E6H4) against the recombinant protein.

(c) Examples of negative sera (1 and 2).

(d) p16$^{INK4a}$ serum reactivity before (1) and after (2) preincubation of serum with recombinant p16$^{INK4a}$. (3) Detection of p16$^{INK4a}$ protein precipitated by serum obtained from a cervical cancer patient and detected by a directly HRP-labeled monoclonal p16$^{INK4a}$ antibody (from (Reuschenbach et al., 2008).

DETAILED DESCRIPTION OF THE INVENTION

The present invention, thus, relates to particular fragments of the cyclin-dependent kinase inhibitor p16$^{Ink4}$ capable of inducing an immune response against p16$^{INK4a}$. An immune response is defined as a condition fulfilling at least one of the following criteria: 1. The induction of CD8-positive T cells, as detectable by cytotoxicity assays or IFN-gamma secretion or perforin expression or granzyme B expression or other cytokines that may be produced by CD8-positive T cells, measurable as above background by ELISpot or intracellular cytokine staining or cytokine ELISA or equivalent methods. 2. The induction of CD4-positive T cells, as detectable by cytokine secretion measurable as above background by ELISpot or intracellular cytokine staining or cytokine ELISA or equivalent methods. Cytokines may comprise IFN-alpha, IFN-gamma, IL-2, IL-4, IL-5, IL-6, IL-10, IL-12, IL-13, IL-17, TNF-alpha, TGF-beta or other cytokines that may be produced by CD4-positive T cells. 3. The induction of antibodies, as detectable by Western blot, ELISA and equivalent or related methods. 4. The induction of any kind of cellular Immune response not mediated by CD8-positive or CD4-positive T cells as described in 1 and 2.

Fragments of p16$^{INK4a}$ are consisting of (a) any one of the following amino acid sequences:

(a$_1$) MEPAAGSSMEPSADWLATAAARGRV; (SEQ ID NO: 1)

(a$_2$) TAAARGRVEEVRALLEAGALPNAPNSY; (SEQ ID NO: 2)

(a$_3$) LPNAPNSYGRRPIQVMMMGSARVAELL; (SEQ ID NO: 3)

(a$_4$) VMMMGSARVAELLLLHGAEPNCADPATLTR; (SEQ ID NO: 4)

(a$_5$) ADPATLTRPVHDAAREGFLDTLVVLHRAGARL; (SEQ ID NO: 5)

(a$_6$) HRAGARLDVRDAWGRLPVDLAEELGHRDVAR; (SEQ ID NO: 6)

(a$_7$) GHRDVARYLRAAAGGTRGSNHARIDAAEGPSDIPD; (SEQ ID NO: 7)

(b) a functional equivalent of the fragment of (a) which is still capable of inducing an immune response against p16$^{INK4a}$; or (c) a combination of fragments of (a) and/or (b).

The term "functional equivalent" as used herein relates to, e.g., variants or fragments of (a) which are still capable of inducing an immune response against p16$^{INK4a}$, thus, are still useful as an efficient vaccine. The variants are characterized by amino acid deletions, substitutions, and/or additions. Preferably, amino acid differences are due to one or more conservative amino acid substitutions. The term "conservative amino acid substitutions" involves replacement of the aliphatic or hydrophobic amino acids Ala, Val, Leu and Be; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

For the generation of peptides showing a particular degree of identity, e.g., genetic engineering can be used to introduce amino acid changes at specific positions of a cloned DNA sequence to identify regions critical for peptide function. For example, site directed mutagenesis or alanine-scanning mutagenesis (introduction of single alanine mutations at every residue in the molecule) can be used (Cunningham and Wells, 1989). The resulting mutant molecules can then be tested for immunogenicity using the assays of the examples.

Preferably, the variants are characterized by not more than 8 aa, more preferably by not more than 6 aa and, even more preferably, by not more than 4 aa substitutions, deletions and/or additions.

In the fragment of the original p16$^{Ink4a}$-fragment at least 5 contiguous aa, preferably at least 10 contiguous aa, more preferably at least contiguous 15 aa and even more preferably at least 20 contiguous aa of the particular amino acid sequence are left. Such fragment is still capable of inducing an immune response against p16$^{INK4a}$ and, thus, is still useful as an efficient vaccine.

The present invention also provides a nucleic acid encoding a fragment of the invention or a vector containing such nucleic acid. The direct injection of genetic material into a living host causes a small amount of its cells to produce the introduced gene products. This inappropriate gene expression within the host has important immunological consequences, resulting in the specific immune activation of the host against the gene delivered antigen. Direct injection of naked plasmid DNA induces strong immune responses to the antigen encoded by the gene vaccine. Once the plasmid DNA construct is injected the host cells take up the foreign DNA, expressing the viral gene and producing $p16^{INK4a}$ inside the cell. This form of antigen presentation and processing induces both MHC and class I and class II restricted cellular and humoral immune responses. The DNA vaccines are composed of vectors normally containing two unites: the antigen expression unit composed of promoter/enhancer sequences, followed by antigen (FSP)-encoding and polyadenylation sequences and the production unit composed of sequences necessary for vector amplification and selection. The construction of vectors with vaccine inserts is accomplished using recombinant DNA technology and the person skilled in the art knows vectors that can be used for this approach. The efficiency of DNA immunization can be improved by stabilising DNA against degradation, and increasing the efficiency of delivery of DNA into antigen presenting cells. This has been demonstrated by coating biodegradable cationic microparticles (such as poly(lactide-co-glycolide) formulated with cetyltrimethylammonium bromide) with DNA. Such DNA-coated microparticles can be as effective at raising CTL as recombinant vaccinia viruses, especially when mixed with alum. Particles 300 nm in diameter appear to be most efficient for uptake by antigen presenting cells.

A variety of expression vectors, e.g., plasmids or viral vectors, may be utilised to contain and express nucleic acid sequences encoding a fragment of the present invention.

A preferred viral vector is a poxvirus, adenovirus, retrovirus, herpesvirus or adeno-associated virus (AAV). Particularly preferred poxviruses are a vaccinia virus, NYVAC, avipox virus, canarypox virus, ALVAC, ALVAC(2), fowlpox virus or TROVAC.

Recombinant alphavirus-based vectors have also been used to improve DNA vaccination efficiency. The gene encoding the fragment of the invention is inserted into the alphavirus replicon, replacing structural genes but leaving non-structural replicase genes intact. The Sindbis virus and Semliki Forest virus have been used to build recombinant alphavirus replicons. Unlike conventional DNA vaccinations, however, alphavirus vectors are only transiently expressed. Alphavirus replicons raise an immune response due to the high levels of protein expressed by this vector, replicon-induced cytokine responses, or replicon-induced apoptosis leading to enhanced antigen uptake by dendritic cells.

The present invention also provides a pharmaceutical composition containing a fragment, nucleic acid sequence or vector of the present invention in an amount suitable for immunization of an individual and, preferably, one or more common auxiliary agents. Such a fragment, nucleic acid sequence or vector can be present as such or in combination with carriers. It is favourable for the carriers in the individual not to be immunogenic. Such carriers may be the individual's own proteins or foreign proteins or fragments thereof. Carriers, such as serum albumin, fibrinogen or transferrin or a fragment thereof are preferred. The fragments contain epitopes which are recognized by cytotoxic T cells, e.g. CD8+ T cells or CD4 T cells, and may induce an immune response. Such epitopes of cell cycle regulatory proteins can be determined by methods with which a person skilled in the art is familiar. It can also be advantageous that various fragments are simultaneously present. For the recombinant production of the above fragments, reference is made, e.g., to Sambrook et al., Molecular Cloning: A Laboratory Manual, 2$^{nd}$ edition, Cold Spring Harbour Laboratory Press, Cold Spring Harbor N.Y. (1989).

The present invention also relates to the use of a fragment, nucleic acid sequence or vector of the present invention for the production of a vaccine for preventing or treating a $p16^{INK4a}$-expressing pre-neoplasia, neoplasia or carcinoma (including an advanced carcinoma).

For example, these may be HPV-induced, $p16^{INK4a}$-expressing anogenital carcinomas, in particular cervical carcinoma, or head and neck cancer and non HPV-induced $p16^{INK4a}$-expressing tumors. Likewise benign modifications such as papillomas, adenomas, hyperplasias or similar proliferations of epithelial, mesenchymal or hematopoietic proliferations are also to be counted there among.

The employed term "individual" comprises an individual of any kind and being able to fall ill with carcinomas. Examples of such individuals are humans and animals as well as cells thereof.

The employed term "amount suitable for immunization of an individual" comprises any amount of a fragment of the invention, to which the above explanations apply correspondingly and with which an individual can be immunized. For example, the amount depends on whether immunization is intended as a prophylactic or therapeutic treatment. In addition, the individual's age, sex and weight play a role for determining the amount. It is favourable to give the individual 100 µg to 1 g of a p16 fragment by means of injection. The injection may be made at various sites of the individual intramuscularly, subcutaneously, intradermally or in any other form of application. It may also be favourable to carry out one or more "booster injections" having about equal amount. In this case, it may be particularly favourable to use different fragments of the respective cell cycle regulatory proteins for the individual injections.

The employed term "common auxiliary agents" comprises any auxiliary agents suitable for a pharmaceutical composition to immunize an individual. Such auxiliary agents are, e.g., immunization adjuvants, such as GM-CSF or Freund's adjuvant, buffered common salt solutions, water, emulsions, such as oil/water emulsions, wetting agents, sterile solutions, etc.

By means of the present invention it is possible to immunize individuals, in particular humans and animals. Immunization takes place by both induction of antibodies and stimulation of T cells. Thus, it is possible to take prophylactic and therapeutic steps against pre-neoplasias, neoplasias and carcinomas.

The invention is explained by the below examples.

Example 1

T Cell Reactivity Against $p16^{INK4a}$ Peptides in Patients with HPV-Associated Neoplasia In order to evaluate whether and to what extent patients with HPV-associated tumors raise T cell responses against the strongly overexpressed $p16^{INK4a}$, different methods were applied which allow for a detailed characterization of immune responses against the $p16^{INK4a}$ antigen. The finding of spontaneous immune responses against $p16^{INK4a}$ in cervical cancer patients proves the immunogenicity of the antigen in general and the particular p16INK4a fragments and provides the rational for immunizing patients with p16$^{INK4a}$ expressing tumors with the p16INK4a fragments.

Peripheral blood mononuclear cells (PBMCs) from 13 women with p16$^{INK4a}$-expressing high grade cervical dysplasia (CIN2/3) were incubated with p16$^{INK4a}$ peptides (Table 1) to determine the proliferative capacity of the immune cells by applying a BrdU assay as a global measure for lymphoproliferative potential after challenge with the p16$^{INK4a}$ peptides. The BrdU-assay is a colorimetric immunoassay applied for the quantification of cell proliferation based on the measurement of the thymidine analogue 5-bromo-2'-deoxyuridine incorporation during DNA synthesis. PBMCs in IMDM medium supplemented with 10% human serum were seeded in a 96-well-microtiter-plate (flat bottom) at a density of 150.000 cells/50 µl/well. Cells in each 4 replicate wells were incubated in the presence of the seven p16INK4a peptides (Table 1), tetanus toxoid (20 ng/ml, Calbiochem, La Jolla, Calif.) and mitogen PHA-L (5 µg/ml, Roche, Mannheim, Germany) as positive controls and no antigen as negative control for 6 days at 37° C., 5% CO2. On day 6, 10 µl/well of BrdU labelling solution (all BrdU assay reagents were used from the Cell Proliferation ELISA, BrdU (colorimetric) by Roche, Mannheim, Germany) diluted 1:100 in IMDM medium+10% human serum were added to each well and incubated for an additional period of 18 hours at 37° C., 5% CO2. On day 7, the plate was centrifuged at 1200 rpm for 10 min and 50 µl of the supernatant was removed and transferred to a new V-bottom plate to be finally stored at −80° C. for cytokine analysis. The remaining cells were dried by using a hair dryer for about 15 minutes and 150 µl/well FixDenat solution were added to the cells and incubated for 30 minutes at room temperature before removing FixDenat by flicking off and tapping carefully. 100 µl/well anti-BrdU-POD working solution were added and incubated for 90 minutes at room temperature, then removed and replaced by 100 µl TMB substrate, which was incubated for 30 minutes at room temperature. The enzyme reaction was stopped by adding 25 µl/well 1N $H_2SO_4$ and optical density (OD) was measured at 450 nm (reference wavelength 620 nm). Cut-off for positive reactions was set as three times standard deviation of ODs in the negative control wells without antigen. PBMCs from 3 out of the 13 tested women showed proliferation in response to the p16$^{INK4a}$ peptides, indicating that incubation with the peptides has activated proliferative memory T cell responses. Overall the pattern of response inducing peptides was heterogenic, indicating various T cell epitopes within the p16 antigen. One patient showed response to peptides p16INK4a_18-44, p16INK4a_37-63, p16INK4a_73-107 and p16INK4a_123-156 one patient to peptides p16INK4a_51-80 and p16INK4a_98-128 and one patients to peptides p16INK4a_1-25 and p16INK4a_37-63 (FIG. 4).

In order to prove that particular p16 fragments are able to induce interferon gamma secretion as one sign for a Th1 response, T cells from 23 patients with invasive cervical cancer and high grade precancerous lesions (CIN2/3) with strong p16$^{INK4a}$ overexpression were tested against the seven p16$^{INK4a}$ peptides (Table 1) in interferon gamma ELISpot assays. T cells were separated from heparinized blood using Ficoll centrifugation, plastic adherence and antibody coupled magnetic beads (CD11, CD16, CD19, CD36, CD56, Pan T cell isolation Kit, Milteny, Bergisch Gladbach, Germany). Dendritic cells were generated by culturing plastic adherent cells for 7 days with IL4 and GM-SCF (each 1000 U/ml) and used as antigen presenting cells in the ELIspot. Each $10^5$ T cells were tested after a short (2 to 5 days) in vitro presensitization with the respective peptide presented by $2 \times 10^4$ dendritic cells.

When subtracting background (2 times the spots in the negative control well+2 standard deviations of reactivity against the respective p16$^{INK4a}$ peptide) in 7 cervical cancer patients T cells (CD4 or CD8) reacting against the p16INK4a_37-63 peptide could be identified (FIG. 2).

Example 2

In Vitro Priming of Healthy Donor T Cells with p16$^{INK4a}$ Peptides

Seven long 25-35mer peptides covering the entire p16$^{INK4a}$ amino acid sequence, each with a 7-13 amino acid overlap were tested to define p16$^{INK4a}$ fragments which are able to induce interferon gamma secreting T cells from healthy donors in vitro. (Table 1).

TABLE 1

Seven overlapping p16$^{INK4a}$ peptides used in in vitro experiments

| SEQ ID No. | peptide | amino acid sequence |
|---|---|---|
| 1 | p16INK4a_1-25 | MEPAAGSSMEPSADWLATAAARGRV |
| 2 | p16INK4a_18-44 | TAAARGRVEEVRALLEAGALPNAPNSY |
| 3 | p16INK4a_37-63 | LPNAPNSYGRRPIQVMMMGSARVAELL |
| 4 | p16INK4a_51-80 | VMMMGSARVAELLLLHGAEPNCADPATLTR |
| 5 | p16INK4a_73-104 | ADPATLTRPVHDAAREGFLDTLVVLHRAGARL |
| 6 | p16INK4a_98-128 | HRAGARLDVRDAWGRLPVDLAEELGHRDVAR |
| 7 | p16INK4a_123-156 | GHRDVARYLRAAAGGTRGSNHARIDAAEGPSDIPD |

In order to show that p16$^{INK4a}$ fragments can stimulate healthy donor T cells in vitro to secrete interferon gamma and to identify the most immunogenic p16$^{INK4a}$ derived epitopes, it was investigated whether T cells isolated from peripheral blood of healthy donors can be stimulated in vitro with these p16$^{INK4a}$ peptides. If the p16$^{INK4a}$ peptides are able to induce a specific T cell response in cell culture experiments, the T cells secrete cytokines when challenged with the respective p16$^{INK4a}$ peptide in so called ELISpot experiments. In ELISpot assays the cytokines (interferon gamma) can be detected by specific antibodies with a subsequent colour reaction.

Peripheral blood mononuclear cells (PBMC) were isolated from heparinized blood (100 ml) of one healthy donor by a Ficoll Plaque gradient density centrifugation. 5 to $10 \times 10^7$ PBMC were separated into monocytes and T cells by plastic adherence and antibody coupled magnetic beads (CD11, CD16, CD19, CD36, CD56, Pan T cell isolation Kit, Milteny, Bergisch Gladbach, Germany). The monocytes were cultured over 7 days with GM-CSF and IL-4 (each 1000 U/ml) to generate antigen presenting dendritic cells.

$2 \times 10^7$ T cells were incubated with $2 \times 10^6$ dendritic cells that were prior pulsed with the p16$^{INK4a}$ peptides (10 µg/ml)

for 4 hours to achieve presentation of the antigens. For each of the 7 p16$^{INK4a}$ peptides a separate stimulation approach was processed.

The T cells were re-stimulated with p16$^{INK4a}$ peptide pulsed dendritic cells and treated with IL-2 and IL-7 (10 U/ml) every 7 days over a 5 week period.

The p16$^{INK4a}$ peptide specific T cell response was measured in interferon gamma ELISpot assays before the stimulations (day 0) and after the last stimulation (day 35). For ELISpot assays, 96 well nitrocellulose plates (MAHA N4550 Millipore) were coated with anti-interferon gamma antibody 1-D1K (Mabtech, Nacka Strand, Sweden) at a concentration of 0.75 ug/well. Each $10^5$ T cells were tested with the respective peptide presented by $2\times10^4$ dendritic cells. After 12 hours incubation at 37° C., detection of secreted interferon gamma was achieved by detection with a biotinylated secondary anti-interferon gamma antibody 7BG-1 (Mabtech), streptavidin-alkaline phosphatase conjugate and BCIP/NBT substrate solution (Sigma Aldrich, St. Louis, USA).

Figure 1:
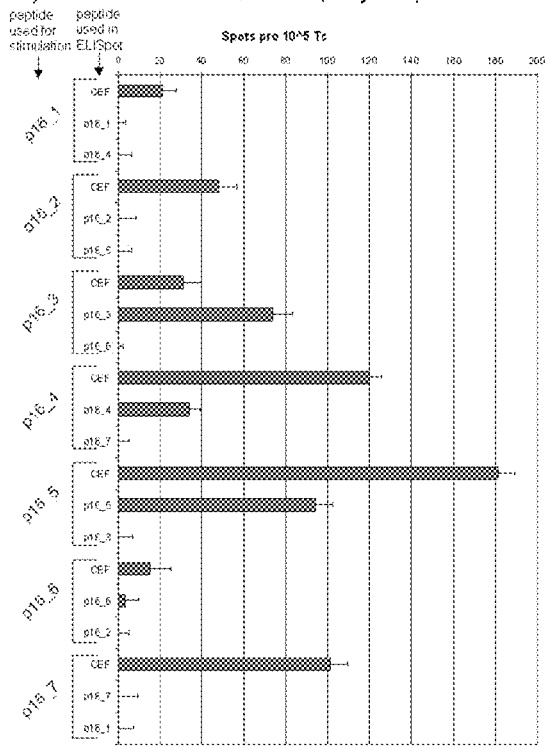
FIG. 1 shows ELISpot (interferon gamma) results before (A) and after (B) stimulation of donor T cells with the p16$^{INK4a}$ peptides.

While no reactivity was detectable on day 0 against any of the seven p16$^{INK4a}$ peptides but only against a virus peptide mix (CEF=CMV & EBV & flu) used as positive control, on day 35 the T cells stimulated with peptides p16INK4a_37-63, p16INK4a_51-80 and p16INK4a_73-104 showed an increased interferon gamma secretion in the ELISpot when tested against target cells pulsed with the respective p16$^{INK4a}$ peptides but not when tested against cells pulsed with the remaining p16$^{INK4a}$ peptides (FIG. 1).

Example 3

Lysis of Cervical Cancer Cell Lines by p16$^{INK4a}$ Reactive T Cells

The ability of activated T cells to lyze p16$^{INK4a}$ expressing cervical cancer cells was tested by chromium release assays using different cervical cancer cell lines as well as HLA matched B cells loaded with p16$^{INK4a}$ peptides as targets. 10×6 target cells (peptide loaded HLA-matched B cells, B cells without peptide) were incubated for 1 hour with $^{51}$Cr (100 μCi) and afterwards with different ratios of T cells from one representative cervical cancer patient that reacted against target cells loaded with the peptide p16INK4a_37-63 in ELIspot assays. Specific lysis of target cells by the T cells can be measured by detection of released radioactivity.

It could be shown that the CD8+ T cells of a cervical cancer patient that reacted against target cells loaded with the peptide p16INK4a_37-63 in ELIspot assays were able to lyse HLA-matched and p16INK4a_37-63-peptide loaded B cells as well as the cervical cancer cell lines HeLa and Caski (both HPV and p16$^{INK4a}$ positive), while no lysis could be detected with the same HLA-matched B cells without the p16INK4a_37-63 peptide and other HPV- and p16$^{INK4a}$ negative cell lines (FIG. 3). These results demonstrate the cytotoxic activity of p16$^{INK4a}$-peptide specific T cells and demonstrate that p16$^{INK4a}$-epitopes are presented on cervical cancer cells and recognized by patient's p16$^{INK4a}$ reactive T cell clones.

Example 4

Humoral Immune Response Against p16$^{INK4a}$

The analysis of over 900 sera further demonstrated that a fraction of individuals develops antibodies that specifically bind to p16$^{INK4a}$ derived epitopes (FIG. 4) (Reuschenbach et al., 2008), which shows the ability of p16$^{INK4a}$ to induce humoral immune responses.

Further is was demonstrated, that also against the peptide p16INK4a_37-63 which appeared to induce the strongest interferon gamma secretion by T cells in vitro, antibodies can be detected in sera. A total of 374 sera from patients with cervical cancer, small cell lung cancer, head and neck cancer and healthy individuals were tested in peptide ELISAs. The peptide (20 ug/ml) was coated to 96 well microtiter plates (Maxisorp, Nunc, Roskilde, Denmark) over night at 4° C., non-specific bindings sites were blocked with 0.5% casein and the sera were tested 1:100 for antibodies against the peptide. Bound serum antibodies were detected by HRP-conjugated anti-human IgG antibody (Jackson Immuno, West Grove, USA and TMB substrate (Sigma Aldrich, St. Louis, USA). At a cut off of a background normalized optical density of 0.03, 15% (56/374) of the tested sera had antibodies against p16INK4a_37-63.

Taken together, these observations demonstrate that patients suffering from HR-HPV-induced dysplasia or neoplasia are capable to develop an anti-p16$^{INK4a}$-immune response. If this immune response would be capable to eliminate HR-HPV transformed cells, the p16$^{INK4a}$ antigen might represent a very attractive candidate for forthcoming vaccines to prevent and/or treat p16INK4a-expressing (pre)-neoplasia, particularly HR-HPV-induced tumors.

LIST OF REFERENCES

Beauséjour, C. M., Krtolica, A., Galimi, F., Narita, M., Lowe, S. W., Yaswen, P., and Campisi, J. (2003). Reversal of human cellular senescence: roles of the p53 and p16 pathways. EMBO J 22, 4212.

Cunningham and Wells, Science 244 (1989), 1081-1085.

Finn, O. J. (2008). Cancer immunology. N. Engl. J. Med. 358, 2704-2715.

Hildesheim, A., Herrero, R., Wacholder, S., Rodriguez, A. C., Solomon, D., Bratti, M. C., Schiller, J. T., Gonzalez, P., Dubin, G., Porras, C., Jimenez, S. E., and Lowy, D. R. (2007). Effect of human papillomavirus 16/18 L1 virus-like particle vaccine among young women with preexisting infection: a randomized trial. JAMA 298, 743-753.

Jäger, E., Jäger, D., and Knuth, A. (2003). Antigen-specific immunotherapy and cancer vaccines. Int J Cancer 106, 817-20.

Klaes, R., Friedrich, T., Spitkovsky, D., Ridder, R., Rudy, W., Petry, U., Dallenbach-Hellweg, G., Schmidt, D., and Knebel Doeberitz, M. (2001). Overexpression of p16 (INK4A) as a specific marker for dysplastic and neoplastic epithelial cells of the cervix uteri. Int J Cancer 92, 276.

Parkin, D. M. and Bray, F. (2006). Chapter 2: The burden of HPV-related cancers. Vaccine 24 Suppl 3, S11-S25.

Rescigno, M., Avogadri, F., and Curigliano, G. (2007). Challenges and prospects of immunotherapy as cancer treatment. Biochim. Biophys. Acta 1776, 108-123.

Reuschenbach, M., Waterboer, T., Wallin, K. L., Einenkel, J., Dillner, J., Hamsikova, E., Eschenbach, D., Zimmer, H., Heilig, B., Kopitz, J., Pawlita, M., Doeberitz, M. K., and Wentzensen, N. (2008). Characterization of humoral immune responses against p16, p53, HPV16 E6 and HPV16 E7 in patients with HPV-associated cancers. Int. J. Cancer 123, 2626-2631.

Sano, T., Oyama, T., Kashiwabara, K., Fukuda, T., and Nakajima, T. (1998). Expression status of p16 protein is associated with human papillomavirus oncogenic potential in cervical and genital lesions. Am. J. Pathol. 153, 1741-1748.

Schadlich, L., Senger, T., Gerlach, B., Mucke, N., Klein, C., Bravo, I. G., Muller, M., and Gissmann, L. (2009). Analysis of modified human papillomavirus type 16 L1 capsomeres: the ability to assemble into larger particles correlates with higher immunogenicity. J. Virol. 83, 7690-7705.

Ishikawa M, Fujii T, Saito M, Nindl I, Ono A, Kubushiro K et al. Overexpression of p16 INK4a as an indicator for human papillomavirus oncogenic activity in cervical squamous neoplasia. Int J Gynecol Cancer 2006; 16(1): 347-353.

Samama B, Lipsker D, Boehm N. p16 expression in relation to human papillomavirus in anogenital lesions. Hum Pathol 2006; 37(5):513-519.

Missaoui N, Hmissa S, Frappart L, Trabelsi A, Ben Abdelkader A, Traore C et al. p16INK4A overexpression and HPV infection in uterine cervix adenocarcinoma. Virchows Arch 2006; 448(5):597-603.

Santos M, Landolfi S, Olivella A, Lloveras B, Klaustermeier J, Suarez H et al. p16 overexpression identifies HPV-positive vulvar squamous cell carcinomas. Am J Surg Pathol 2006; 30(11):1347-1356.

Roma A A, Goldblum J R, Fazio V, Yang B. Expression of 14-3-3sigma, p16 and p53 proteins in anal squamous intraepithelial neoplasm and squamous cell carcinoma. Int J Clin Exp Pathol 2008; 1(5):419-425.

Hafkamp H C, Speel E J M, Haesevoets A, Bot F J, Dinjens W N M, Ramaekers F C S et al. A subset of head and neck squamous cell carcinomas exhibits integration of HPV 16/18 DNA and overexpression of p16INK4A and p53 in the absence of mutations in p53 exons 5-8. Int J Cancer 2003; 107(3):394.

Nindl I, Meyer T, Schmook T, Ulrich C, Ridder R, Audring H et al. Human papillomavirus and overexpression of P16INK4a in nonmelanoma skin cancer. Dermatol Surg 2004; 30(3):409-414.

Busch C, Geisler J, Knappskog S, Lillehaug J R, Lønning PE. Alterations in the p53 pathway and p16INK4a expression predict overall survival in metastatic melanoma patients treated with dacarbazine. J Invest Dermatol. 2010 October; 130(10):2514-6.

Giordano G, Azzoni C, D'Adda T, Rocco A, Gnetti L, Froio E et al. Human papilloma virus (HPV) status, p16INK4a, and p53 overexpression in epithelial malignant and borderline ovarian neoplasms. Pathol Res Pract 2008; 204 (3):163-174.

Giordano G, Azzoni C, D'Adda T, Merisio C. P16(INK4a) overexpression independent of Human Papilloma Virus (HPV) infection in rare subtypes of endometrial carcinomas. Pathol Res Pract. 2007; 203(7):533-8.

Di Vinci A, Perdelli L, Banelli B, Salvi S, Casciano I, Gelvi I, Allemanni G, Margallo E, Gatteschi B, Romani M. p16(INK4a) promoter methylation and protein expression in breast fibroadenoma and carcinoma. Int J Cancer. 2005 Apr. 10; 114(3):414-21.

Buza N, Cohen P J, Pei Hui, Parkash V. Inverse p16 and p63 expression in small cell carcinoma and high-grade urothelial cell carcinoma of the urinary bladder. Int J Surg Pathol. 2010 April; 18 (2):94-102.

Esposito V, Baldi A, Tonini G, Vincenzi B, Santini M, Ambrogi V, Mineo T C, Persichetti P, Liuzzi G, Montesarchio V, Wolner E, Baldi F, Groeger A M. Analysis of cell cycle regulator proteins in non-small cell lung cancer. J Clin Pathol. 2004 January; 57(1):58-63.

Ikuerowo S O, Kuczyk M A, von Wasielewski R, shitu OB, Jonas U, Machtens S, Serth J. p16INK4a expression and clinicopathologic parameters in renal cell carcinoma. Eur Urol. 2007 March; 51(3):732-7; discussion 738. Epub 2006 Aug. 23.

Leversha M A, Fielding P, Watson S, Gosney J R, Field J K. Expression of p53, pRB, and p16 in lung tumours: a validation study on tissue microarrays. J Pathol. 2003 August; 200(5):610-9.

Ding G C, Ren J L, Chang F B, Li J L, Yuan L, Song X, Zhou S L, Guo T, Fan Z M, Zeng Y, Wang L D. Human papillomavirus DNA and P16(INK4A) expression in concurrent esophageal and gastric cardia cancers. World J Gastroenterol. 2010 Dec. 14; 16(46):5901-6.

Kim B N, Yamamoto H, Ikeda K, Damdinsuren B, Sugita Y, Ngan C Y, Fujie Y, Ogawa M, Hata T, Ikeda M, Ohue M, Sekimoto M, Monden T, Matsuura N, Monden M. Methylation and expression of p16INK4 tumor suppressor gene in primary colorectal cancer tissues. Int J Oncol. 2005 May; 26(5):1217-26.

Okamoto A, Demetrick D J, Spillare E A, Hagiwara K, Hussain S P, Bennett W P, Forrester K, Gerwin B, Greenblatt M S, Serrano M. p16INK4 mutations and altered expression in human tumors and cell lines. Cold Spring Harb Symp Quant Biol 1994; 59:49-57.

What is claimed is:

1. A vector comprising a nucleic acid sequence encoding a fragment of the cyclin-dependent kinase inhibitor p16INK4 capable of inducing an immune response against p16INK4a, wherein said nucleic acid sequence encodes:

(a) any one of the following amino acid sequences:

```
                                    (SEQ ID NO: 1)
(a1)    MEPAAGSSMEPSADWLATAAARGRV;

(SEQ ID NO: 2)
(a2)    TAAARGRVEEVRALLEAGALPNAPNSY;

(SEQ ID NO: 3)
(a3)    LPNAPNSYGRRPIQVMMMGSARVAELL;

(SEQ ID NO: 4)
(a4)    VMMMGSARVAELLLLHGAEPNCADPATLTR;

(SEQ ID NO: 5)
(a5)    ADPATLTRPVHDAAREGFLDTLVVLHRAGARL;

(SEQ ID NO: 6)
(a6)    HRAGARLDVRDAWGRLPVDLAEELGHRDVAR;

(SEQ ID NO: 7)
(a7)    GHRDVARYLRAAAGGTRGSNHARIDAAEGPSDIPD;
```

(b) a combination of the amino acid sequences of (a).

2. The vector of claim 1, wherein said vector is a plasmid or viral vector.

3. The viral vector of claim 2, wherein said viral vector is a poxvirus, adenovirus, retrovirus, herpesvirus, alphavirus-based vector or adeno-associated virus (AAV).

4. The viral vector of claim 3, wherein said poxvirus is a vaccinia virus, NYVAC, avipox virus, canarypox virus, ALVAC, ALVAC(2), fowlpox virus or TROVAC.

5. A pharmaceutical composition containing the vector of claim 1.

6. The vector according to claim 1, further comprising additional nucleic acid sequences for amplification and selection.

7. The vector according to claim 6, wherein the additional nucleic acid sequences are selected from the group consisting of promoter sequences, enhancer sequences, and polyadenylation sequences.

* * * * *

SEQUENCE LISTING

```
<160> NUMBER OF SEQ ID NOS: 7

<210> SEQ ID NO 1
<211> LENGTH: 25
<212> TYPE: PRT
<213> ORGANISM: Homo sapiens
<220> FEATURE:
<221> NAME/KEY: SOURCE
<222> LOCATION: (1)..(25)
<223> OTHER INFORMATION: p16INK4A fragment

<400> SEQUENCE: 1

Met Glu Pro Ala Ala Gly Ser Ser Met Glu Pro Ser Ala Asp Trp Leu
1               5                   10                  15

Ala Thr Ala Ala Ala Arg Gly Arg Val
            20                  25
```

-continued

```
<210> SEQ ID NO 2
<211> LENGTH: 27
<212> TYPE: PRT
<213> ORGANISM: Homo sapiens
<220> FEATURE:
<221> NAME/KEY: SOURCE
<222> LOCATION: (1)..(27)
<223> OTHER INFORMATION: pINK4A fragment

<400> SEQUENCE: 2

Thr Ala Ala Ala Arg Gly Arg Val Glu Glu Val Arg Ala Leu Leu Glu
1               5                   10                  15

Ala Gly Ala Leu Pro Asn Ala Pro Asn Ser Tyr
            20                  25

<210> SEQ ID NO 3
<211> LENGTH: 27
<212> TYPE: PRT
<213> ORGANISM: Homo sapiens
<220> FEATURE:
<221> NAME/KEY: SOURCE
<222> LOCATION: (1)..(27)
<223> OTHER INFORMATION: pINK4A fragment

<400> SEQUENCE: 3

Leu Pro Asn Ala Pro Asn Ser Tyr Gly Arg Arg Pro Ile Gln Val Met
1               5                   10                  15

Met Met Gly Ser Ala Arg Val Ala Glu Leu Leu
            20                  25

<210> SEQ ID NO 4
<211> LENGTH: 30
<212> TYPE: PRT
<213> ORGANISM: Homo sapiens
<220> FEATURE:
<221> NAME/KEY: SOURCE
<222> LOCATION: (1)..(30)
<223> OTHER INFORMATION: pINK4A fragment

<400> SEQUENCE: 4

Val Met Met Met Gly Ser Ala Arg Val Ala Glu Leu Leu Leu Leu His
1               5                   10                  15

Gly Ala Glu Pro Asn Cys Ala Asp Pro Ala Thr Leu Thr Arg
            20                  25                  30

<210> SEQ ID NO 5
<211> LENGTH: 32
<212> TYPE: PRT
<213> ORGANISM: Homo sapiens
<220> FEATURE:
<221> NAME/KEY: SOURCE
<222> LOCATION: (1)..(32)
<223> OTHER INFORMATION: p16INK4A fragment

<400> SEQUENCE: 5

Ala Asp Pro Ala Thr Leu Thr Arg Pro Val His Asp Ala Ala Arg Glu
1               5                   10                  15

Gly Phe Leu Asp Thr Leu Val Val Leu His Arg Ala Gly Ala Arg Leu
            20                  25                  30

<210> SEQ ID NO 6
<211> LENGTH: 31
<212> TYPE: PRT
<213> ORGANISM: Homo sapiens
<220> FEATURE:
<221> NAME/KEY: SOURCE
<222> LOCATION: (1)..(31)
```

```
<223> OTHER INFORMATION: p16INK4A fragment

<400> SEQUENCE: 6

His Arg Ala Gly Ala Arg Leu Asp Val Arg Asp Ala Trp Gly Arg Leu
1               5                   10                  15

Pro Val Asp Leu Ala Glu Glu Leu Gly His Arg Asp Val Ala Arg
            20                  25                  30

<210> SEQ ID NO 7
<211> LENGTH: 35
<212> TYPE: PRT
<213> ORGANISM: Homo sapiens
<220> FEATURE:
<221> NAME/KEY: SOURCE
<222> LOCATION: (1)..(35)
<223> OTHER INFORMATION: p16INK4A fragment

<400> SEQUENCE: 7

Gly His Arg Asp Val Ala Arg Tyr Leu Arg Ala Ala Ala Gly Gly Thr
1               5                   10                  15

Arg Gly Ser Asn His Ala Arg Ile Asp Ala Ala Glu Gly Pro Ser Asp
            20                  25                  30

Ile Pro Asp
        35
```